United States Patent [19]

Wong et al.

[11] Patent Number: 5,340,570
[45] Date of Patent: Aug. 23, 1994

[54] DISPENSING SYSTEM FOR SPRAYABLE GEL-TYPE HAIR CONDITIONER

[75] Inventors: Stephanie Wong, Bridgeport; Teresa Ferullo, Wilton; Thomas M. Schultz, Ridgefield, all of Conn.

[73] Assignee: Shiseido Co., Ltd., Tokyo, Japan

[21] Appl. No.: 26,530

[22] Filed: Mar. 4, 1993

Related U.S. Application Data

[63] Continuation of Ser. No. 793,157, Nov. 18, 1991, abandoned.

[51] Int. Cl.$^5$ .............................................. A61K 7/06
[52] U.S. Cl. .................................. 424/71; 222/321; 239/394; 239/490; 424/70; 424/401; 424/DIG. 2; 514/944
[58] Field of Search ............. 424/71, 70, 401, DIG. 2; 222/321; 239/394, 490; 514/944

[56] References Cited

U.S. PATENT DOCUMENTS

| | | | |
|---|---|---|---|
| 3,246,850 | 4/1966 | Bourke | 239/394 |
| 3,724,763 | 4/1973 | Braun | 239/490 |
| 4,563,347 | 1/1986 | Starch | 424/70 |
| 4,591,076 | 5/1986 | Iizuka | 222/321 |
| 4,749,732 | 6/1988 | Kohl et al. | 524/43 |
| 5,037,013 | 8/1991 | Howlett | 222/402.2 |
| 5,059,414 | 10/1991 | Dallal et al. | 424/70 |

*Primary Examiner*—Thurman K. Page
*Assistant Examiner*—Robert H. Harrison
*Attorney, Agent, or Firm*—Melvin I. Stoltz

[57] ABSTRACT

By incorporating an alkyl polyol and a water soluble or emulsifiable silicone based compound into a moderately viscous gel-type hair conditioning composition, a hair conditioning gel formulation is attained which is able to be delivered in a spray mist pattern using conventional small diametered pump spray nozzles. Preferably, the alkyl polyol has a carbon content ranging between 2 and 8, and the hydroxyl ion content ranges between 2 and 7 and are not spaced apart by more than 4 carbon atoms. It has been found that by employing this invention, the resulting gel formulation is able to be dispensed consistently, repeatedly and easily in a liquified spray mist through a pump nozzle having apertures ranging between about 0.010 and 0.030 mm.

3 Claims, No Drawings

DISPENSING SYSTEM FOR SPRAYABLE GEL-TYPE HAIR CONDITIONER

RELATED APPLICATION

This application is a continuation of application Ser. No. 07/793,157, filed Nov. 18, 1991, now abandoned.

TECHNICAL FIELD

This invention relates to hair conditioners and, more particularly, to viscous, gel-type hair conditioners formulated for being dispensed by spraying.

BACKGROUND ART

Human hair requires cleaning, since the hair fibers become soiled, both from environmental contamination as well as contamination and soiling from chemical agents produced by the body. Generally, shampooing is employed to clean the hair by removing excess soil and body oils which have built up on the hair fibers. Unfortunately, while being capable of cleaning the hair fibers, shampoos generally leave the hair stripped, over-processed and difficult to manage.

In an attempt to eliminate these problems, various hair conditioning aids have been developed. In fact, hair conditioning aids are numerous and have appeared in almost every conceivable form—liquids, solids, emulsions, aqueous and oil solutions as well as chemicals embedded in flexible substrates which are rubbed throughout the hair to achieve transfer to the hair. Unfortunately, these prior art systems have been unable to attain all of the requirements for a good hair conditioner.

In general, a hair conditioner should be capable of effectively grooming the hair and keeping it in place, thereby leaving the hair natural in appearance, without any evidence that a hair conditioner has been used. Clearly, no oily film should remain on the hair fibers which can act as a dirt catcher. Furthermore, the hair conditioner must leave the hair with a high luster, gloss, sheen, as well as provide the entire head of hair with a full-bodied appearance, with the hair being easily managed and feeling soft and silky.

In addition to being unable to provide all of these qualities, prior art hair conditioners are also typically difficult to thoroughly apply to all of the hair fibers. Furthermore, many prior art compositions are cumbersome to use.

Recently, gel formulations of hair conditioners have become popular. However, due to the viscous nature of these prior art gel-type hair conditioners, these conditioners are typically dispensed directly through the portal of the container and are pumped through a large orifice. Regardless of which type of dispensing system is used, a large quantity of the gel is dispensed into the hands of the beautician or user followed by vigorous rubbing of the hands, in order to liquify the gel.

This process is time consuming, and often leaves the hands of the beautician or the user with an oily film which must be washed off. Any attempt to dispense these prior art gel conditioners through smaller orifices merely causes the orifices to clog and become unusable.

Therefore, it is a principal object of the present invention to provide a hair conditioner having a gel formulation which is capable of being dispensed quickly and easily in a spray form through small diameter orifices.

Another object of the present invention is to provide a gel-type hair conditioner having the characteristic features described above which is capable of being applied directly to the head of hair quickly and easily by merely spraying the gel formulation on the hair.

Another object of the present invention is to provide a gel-type hair conditioner having the characteristic features described above which is capable of being sprayed through conventional, small-diameter pump spray nozzles repeatedly, without clogging the spray orifices, producing a mist-type spray.

Other and more specific objects will in part be obvious and will in part appear hereinafter.

DETAILED DISCLOSURE OF THE INVENTION

The present invention overcomes the prior art difficulties typically encountered with gel-type hair conditioners by attaining a viscous gel formulation which is capable of being dispensed by spraying. By employing the present invention, the prior art difficulties and drawbacks commonly encountered with gel formulations for hair conditioners are totally eliminated and the gel formulation of the present invention is quickly and easily applied to the head of hair by spraying directly on the hair or into the user's hands. Using the present invention, the viscous gel hair conditioner is capable of being dispensed as a spray, passing easily through small diameter orifices.

It has been found that by incorporating alkyl polyols into the gel formulation, a unique gel-type hair conditioner is attained which is capable of being sprayed through conventional, small-diameter pump spray nozzles. In achieving this result, it has been found that the alkyl polyol should have a carbon atom content ranging between 2 and 8, and a hydroxyl ion content ranging between 2 and 7.

In addition, it is preferred that the hydroxyl ions of the alkyl polyol not be vicinal. Furthermore, it has been found that the hydroxyl ions are preferably not spaced apart by more than 4 carbon atoms.

Alkyl polyols which have been found to be effective in attaining the sprayable hair conditioning gel include glycerin, propylene glycol, sorbitol, hydrogenated starch hydrolysate, 1,3-butylene glycol, and diethylene glycol. In Table I, these alkyl polyols are listed along with their empirical formulas.

TABLE I

| Alkyl Polyol | Structural Formula |
| --- | --- |
| Glycerin | $HOCH_2CH(OH)CH_2$ |
| Propylene glycol | $CH_3CH(OH)CH_2OH$ |
| Sorbitol | $HOCH_2(CH_2OH)_4CH_2OH$ |
| Hydrogenated starch hydrolysate | — |
| 1,3-Butylene Glycol | $HOCH_2CH_2CHOHCH_3$ |
| Diethylene Glycol | $HOCH_2CH_2OCH_2CH_2OH$ |

In order to obtain a hair conditioning gel capable of being dispensed as a liquid spray, the gel formulation must contain a water soluble or emulsifiable silicone-based compound in addition to the alkyl polyol. The incorporation of a silicon-based compound provides the hair with added luster and sheen, as well as imparting added lubricity to the hair for increased slip and an increased silky feeling. Furthermore, the silicone-based compound provides a synergistic effect, increasing the action of the other constituents used in the hair treatment composition, and assisting in attaining sprayability of the viscous gel formulation.

Although most water soluble or emulsifiable silicone-based compounds can be employed in the sprayable gel formulation of the present invention, the preferred silicone-based composition comprises amodimethicone. Amodimethicone is a silicone polymer end blocked with amino functional groups. Its formula is represented as follows:

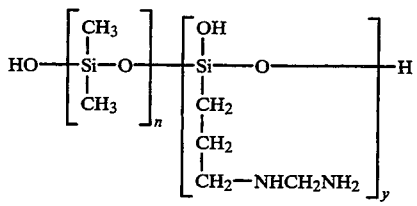

where x has a value of 4 or more.

Although time use of amodimethicone is preferred, other water soluble or emulsifiable silicone-based compounds can be employed, with substantially equal efficacy, without departing from the scope of the present invention. One such alternate compound is dimethicone, which is a mixture of fully methylated linear siloxane polymers end blocked with trimethylsiloxy units. Empirically, the formula for dimethicone is $(C_2H_6OSi)_xC_4H_{12}Si$, with the following being representative of its general formula:

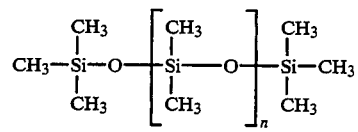

In addition, the silicone-based compound may comprise dimethicone copolyol, which is a polymer of dimethylsiloxane with polyoxyethylene and/or polyoxypropylene side chains. The following represents the general formula for dimethicone copolyol:

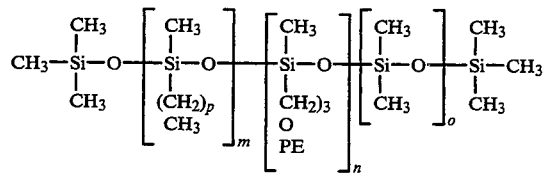

where $PE=(C_2H_4O-) \times (C_3H_6O-)_pH$.

Another silicone compound which can be employed is stearoxytrimethylsilane which is an organo-silicon compound having the empirical formula of $C_{21}H_{45}OSi$. Its formula generally conforms to the following:

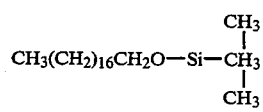

In addition, stearoxy dimethicone can be employed, which is a polymer of dimethylpolysiloxane end blocked with stearoxy groups.

By employing these two principal ingredients in a conventional, viscous gel formulation, the resulting gel composition is capable of being dispensed through small diameter spray nozzles, achieving the delivery of the gel composition as a liquid spray. Prior to this invention, the delivery of viscous gels has only been through large diameter pump means or directly through the container orifice or portal. By employing this invention, easy application of the hair conditioning gel is realized and both uniform and complete application of the hair conditioner to all desired areas is obtained.

By incorporating an alkyl polyol and a water soluble or emulsifiable silicone composition, in a conventional hair conditioning gel formulation, the resulting viscous composition is capable of being dispensed through apertures ranging in size between 0.010 and 0.030 mm with complete ease. Furthermore, by employing a plurality of orifices, a substantially liquid, mist spray pattern is attained, even though the gel composition comprises a viscosity previously incapable of being dispensed in this manner.

Although the preferred alkyl polyols have a viscosity generally ranging between about 9,000 cps and 12,000 cps, and the hair conditioning gel formulations made in accordance with the present invention have viscosities ranging between 1,000 cps and 15,000 cps, the gel formulations of this invention are able to be dispensed as a liquid mist spray, delivered through apertures having a diameter of 0.030 mm or less. In obtaining the desired mist spray in the gel formulation of this nature, the concentration of the alkyl polyol is preferably maintained between about 0.10% and 10% by weight of the gel formulation.

It has been also been found that the water soluble or emulsifiable silicone concentration may range between about 0.02% and 5% by weight of the gel formulation. However, a range of between 0.02% and 1.5% by weight is preferred.

In addition to the use of an alkyl polyol and a water soluble or emulsifiable silicone, as detailed above, it has also been found that a particular mixing procedure is preferably employed in attaining the gel product of this invention. In particular, it has been found that the water based ingredients and the oil based ingredients are preferably separately prepared and intermixed with each other only upon completion of the entire product formulation. By employing this formulation procedure, optimum results have been achieved and a viscous gel product has been produced which easily and consistently dispenses a spray mist pattern through small diameter apertures.

Furthermore, it has been found that the hair conditioning gel formulations of the present invention re-congeal when intermixed after spraying, with the viscosity of the re-congealed gel being between 2% and 15% less than the viscosity of the original hair conditioning gel formulation. This reduction in viscosity provides a further advantage over prior art formulations by providing a dispensed gel-type hair conditioner which is more easily thoroughly spread throughout the entire head of hair.

EXAMPLES

In order to prove the efficacy of the present invention, the following experimental tests were conducted. As is apparent from these experiments, the present invention provides a viscous hair conditioning gel which is easily and consistently delivered through a conventional small diametered apertured pump in a liquid mist spray.

In Table II, a typical hair conditioning gel base formulation is provided. To this gel base, glycerin and dimethicone copolyol were added in the ranges detailed in Table III to produce a plurality of sample products.

TABLE II

Hair Conditioning Gel Base Formulation

| Ingredient | % by Wgt |
| --- | --- |
| PVP/VA | 1.50 |
| Oleth-20 | 0.28 |
| Carbomer 940 | 0.22 |
| Panthenol | 0.20 |
| Methylchloroisothiazolinone or Methylisothiazolinone | 0.06 |
| Fragrance | 0.04 |
| Triethanolamine | 0.16 |
| Deionized Water | q.s. |

TABLE III

| Ingredient | % by Wgt |
| --- | --- |
| Glycerin | 0.10–10 |
| Dimethicone Copolyol | 0.02–5 |

In preparing each hair conditioning gel formulation sample, the following procedure was employed. Initially, a first vessel suitable for making thick slurries and equipped with a variable speed mixer and side scrapers was selected and deionized water was added to the first vessel and agitated rapidly. Then, the carbomer 940 was carefully sifted into the water and mixed until completely hydrated and free of lumps. Typically, this took at least three hours. Once completed, the methylchloroisothiazolinone or the methylisothiazolinone was added and mixed until homogeneous.

In a second vessel, equipped with a variable speed mixer, deionized water was added along with the PVP/VA and rapidly agitated. This mixing continued until the PVP/VA was dissolved and the resulting solution became clear. Then, the desired amount of dimethicone copolyol was added along with the desired amount of glycerin and panthenol. Mixing continued until the solution was homogeneous.

In a third vessel, equipped with a heating jacket, the oleth-20 was added and heated until melted. During this melting process, 50° C. was not exceeded. Once melted, the flagrance was added and mixed until homogeneous. Then, the homogeneous, intermixed fragrance and oleth-20 combination was added to the solution in the second vessel. Mixing then continued until the solution contained therein was homogeneous.

Once the solution in the second vessel was homogeneous, a portion of the triethanolamine was added and mixed until homogeneous. This solution was then allowed to stand until it became clear. Typically, this took at least twenty minutes.

Once the solution in the second vessel was clear, the solution was added to the first vessel under moderate to strong mixing. However, care was taken to incorporate as little air as possible. In addition, the second vessel was rinsed with deionized water and added to the composition in the first vessel.

Mixing continued until the batch product was clear and a moderately viscous gel was attained. Typically, this required a minimum of forty-five minutes. The batch product was then completed by adding deionized water to attain a desired batch product size, and by adding additional triethanolamine to adjust the pH.

When each of the hair conditioning gel formulation samples, with varying quantities of glycerin and dimethicone copolyol were completed, each sample formulation was placed in a container for being dispensed by a finger actuated pump sprayer. In each instance, the finger actuated pump sprayer incorporated orifices having a diameter of 0.013 inches.

Each sample formulation was tested to determine its ability to provide a consistent, repeatable, easily dispensed liquified spray mist pattern. In each instance, the precisely desired spray mist pattern was achieved, clearly showing the efficacy of the present invention.

As part of these experiments, it was noted that compositions containing dimethicone copolyol ranging between 0.02% and 1.5% by weight provided superior sprayable product formulations, as opposed to those products in which the dimethicone copolyol exceeded 1.5%. Although such products were effective in providing a spray mist pattern, a more effective spray was obtained with the dimethicone copolyol at or below 1.5%.

In Table IV, the preferred hair conditioning gel formulation is provided. In preparing this composition, the process detailed above in reference to Tables II and III was employed.

TABLE IV

| Sprayable Gel Formulation | |
|---|---|
| Ingredient | % by Wgt |
| PVP/VA | 1.50 |
| Glycerin | 1.00 |
| Dimethicone Copolyol | 0.70 |
| Oleth-20 | 0.28 |
| Carbomer 940 | 0.22 |
| Panthenol | 0.20 |
| Methylchloroisothiazolinone or Methylisothiazolinone | 0.06 |
| Fragrance | 0.04 |
| Triethanolamine | 0.16 |
| Deionized Water | 95.84 |

In order to further prove the efficacy of the preferred gel formulation detailed in Table IV, as well as to study the sprayability of similar gel formulations employing different alkyl polyols and to evaluate any changes occurring to the gel after spraying, six separate gel samples were constructed. Each sample was identical, except for the alkyl polyol employed, and was manufactured using the process detailed above in reference to Tables II and III.

One sample consisted of the formula detailed in Table IV, while each of the other samples were identical in each and every ingredient and quantity, except for the glycerin. Instead of glycerin, each sample incorporated an identical quantity of one alkyl polyol selected from the group consisting of propylene glycol, sorbitol, hydrogenated starch hydrolysate, 1,3-butylene glycol, and diethylene glycol.

Each of these six samples were separately tested by first measuring the viscosity of each sample formulation and then separately dispensing each formulation through a finger actuated pump sprayer incorporating orifices having a diameter of 0.013 inches. After spraying, the viscosity of each sample was measured again. In each of the viscosity measurements, a Brookfield Viscometer was employed using spindle #2, which was operated at 6 rpm for sixty seconds at 25° C. The viscosity measurement obtained, both before spraying and after spraying, for each of the six samples are shown in Table V.

TABLE V

| Alkyl Polyol used in Gel Sample | Viscosity Measurement | |
|---|---|---|
| | Before Spraying | After Spraying |
| Glycerin | 9700 cps. | 8500 cps. |
| Propylene glycol | 10880 cps. | 9800 cps. |
| Sorbitol | 9700 cps. | 8700 cps. |
| Hydrogenated Starch Hydrolysate | 11400 cps. | 11100 cps. |
| 1,3-Butylene Glycol | 9400 cps. | 8100 cps. |
| Diethylene Glycol | 8900 cps. | 7700 cps. |

As is apparent from the results provided in Table V, each of the samples experienced a reduction in the viscosity after spraying. This shows that each gel product experienced liquification during the spraying process and recongealed after spraying at a lower viscosity. As a result, a more easily managed product was realized, which was able to be applied more quickly and easily onto the hair fibers.

In addition, in each of the tests conducted, the gel product was easily delivered through the sprayer as a liquified mist spray. It was found that the mechanical force acting on the gel caused the gel formula to be liquified as the gel passed through the small diameter orifices of the sprayer head, with the gel recongealing into a viscous form upon recombination. As a result, each sample provided an easily dispensed gel formulation, with each sample, with each sample was dispensed easily, quickly, repeatedly and conveniently, while also being readily spread onto the hair once dispensed.

In order to further prove the efficacy of the present invention and the preferability of the formulation process, a conventional gel-type hair conditioner was tested to determine its ability to be dispensed through a pump-type sprayer of the nature detailed above. In conducting this experimental test program, the gel formulation employed as the base consisted of a commercially available gel product sold under the trade name ULTRA BOND® WELDING GEL™, sold by Zotos International of Darien, Conn.

In this test program, the base gel was tested as commercially available and then diluted with water to reduce its viscosity and retested. Then, various amounts of glycerin and silicone were added to the water diluted base gel to see what effect, if any, the inclusion of the varying amounts of these compounds had on its sprayability. The results of this test program are detailed in Table VI.

TABLE VI

| Gel Base | Viscosity (cps) | Silicone % By Weight | Glycerin % By Weight | Results |
|---|---|---|---|---|
| Welding Gel ™ | >17000 | 0 | 0 | No spray |
| Welding Gel ™ (Diluted with Water) | 8000–17000 | 0 | 0 | Streams |
| Welding Gel ™ (Diluted with Water) | 8000–17000 | 0 | 1–10 | Streams |
| Welding Gel ™ (Diluted with Water) | 8000–17000 | 1–10 | 0 | Sprays with central concentrated stream |
| Welding Gel ™ (Diluted with Water) | 8000–17000 | 1–10 | 1–10 | Sprays with inconsistent mist pattern |

As is apparent from the results of Table VI, the commercially available high viscosity gel formulation was found to be incapable of being delivered through the pump sprayer. The lower viscosity gel formulation produced a product stream when dispensed through the pump sprayer. Similarly, when varying amounts of only glycerin were added to the water diluted gel formulation, only a stream of product was dispensed from the pump. When varying amounts of the silicone compound was added to the water diluted base gel, a spray was produced having a central concentrated stream. No liquified mist spray pattern was realized with any of these formulations.

Finally, when varying amounts of both glycerin and silicone were added to the water-diluted gel base, a sprayable gel formulation was achieved. However, the spray produced did not consistently and repeatedly provide a liquified mist spray pattern, as attained with the sample formulations detailed above. It is believed that this result is due to the addition of the glycerin and silicone to an existing product and the inability to add these ingredients using the preferred formulation process.

For purposes of clarity and consistency, the chemicals detailed herein have been identified using the designations adopted by the Cosmetic, Toiletry and Fragrance Association (CTFA), and detailed in the CTFA Cosmetic Ingredient Dictionary, 4th Edition, Published 1991. In addition, in some instances, the empirical formula and the structural formula have also been provided.

It will thus be seen that the objects set forth above, among those made apparent from the preceding description, are efficiently attained and, since certain changes may be made in the above product formulation without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients whenever the sense permits.

Having described our invention, what we claim is new and desire to secure by Letters Patent is:

1. A product delivery system for dispensing a viscous, hair conditioning gel product in a spray mist form, said delivery system comprising
    A. a container for holding the viscous hair conditioning gel product;
    B. a finger actuated pump
        a. mounted to the container,
        b. incorporating a movable actuator having a plurality of delivery apertures each comprising a diameter ranging between about 0.010 and 0.030 millimeters, and
        c. cooperatively associated with the hair conditioning gel product for delivering the gel product through the plurality of apertures formed in the movable actuator; and
    C. a viscous hair conditioning gel product comprising
        a. hair conditioning ingredients,
        b. between about 0.10% and 10% by weight of the total gel product of an alkyl polyol selected from the group consisting of glycerin, propylene, glycol, sorbitol, hydrogenated starch hydrolysate, 1-3 butylene glycol, and diethylene glycol, c. between about 0.02% and 5% by weight of the total gel product of a water soluble or emulsifiable silicone based compound selected from the group consisting of amodimethicone, dimethicone, dimethicone copolyol, stearoxytrimethylsilane and stearoxy dimethicone; and d. a viscosity ranging between about 1,000 and 15,000 centipoises; whereby a dispensing system is achieved for delivering a viscous hair conditioning gel product in a spray mist form.

2. The product delivery system defined in claim 1, wherein the hair conditioning ingredients comprise the following weight percentages based upon the total gel product:

a. 1.50% by weight of PVP/VA,
b. 0.28% by weight of Oleth-20,
c. 0.22% by weight of carbomer 940,
d. 0.20% by weight of panthenol,
e. 0.06% by weight of at least one selected from the group consisting of methylchloroisothiazolinone and methylisothiazolinone,
f. 0.16% by weight of triethanolamine, and
g. 0.04% by weight of a fragrance.

3. The product delivery system defined in claim 2, wherein the alkyl polyol comprises 1.00% by weight of the total gel product and the silicone-based compound comprises 0.70% by weight of the total gel product.

* * * * *